United States Patent

Schlak et al.

(10) Patent No.: US 6,818,794 B2
(45) Date of Patent: Nov. 16, 2004

(54) EXTRACTION OF KETAZINE SOLUTIONS

(75) Inventors: Ottfried Schlak, Überlingen (DE); Hans-Georg Adams, Leverkusen (DE); Johannes Kaulen, Odenthal (DE)

(73) Assignee: Bayer Aktiengesellschaft, Leverkusen (DE)

(*) Notice: Subject to any disclaimer, the term of this patent is extended or adjusted under 35 U.S.C. 154(b) by 0 days.

(21) Appl. No.: 10/305,458

(22) Filed: Nov. 27, 2002

(65) Prior Publication Data

US 2003/0105355 A1 Jun. 5, 2003

(30) Foreign Application Priority Data

Dec. 3, 2001 (DE) .......................................... 101 59 265

(51) Int. Cl.[7] ..................... C07C 241/00; C07C 249/00; C07C 209/00
(52) U.S. Cl. ........................ 564/249; 564/250; 564/264; 564/464; 564/497
(58) Field of Search .............................. 564/249, 250, 564/264, 464, 497

(56) References Cited

U.S. PATENT DOCUMENTS

| | | | |
|---|---|---|---|
| 3,875,231 A | 4/1975 | Brandl et al. | ............ 260/566 B |
| 4,005,179 A | 1/1977 | Eichenhofer et al. | ....... 423/407 |

FOREIGN PATENT DOCUMENTS

| | | |
|---|---|---|
| DE | 1 273 503 | 7/1968 |
| DE | 1 282 617 | 11/1968 |
| GB | 1191630 | 5/1970 |

*Primary Examiner*—James O. Wilson
*Assistant Examiner*—Sikarl A. Witherspoon
(74) *Attorney, Agent, or Firm*—Godfried R. Akorli; Diderico van Eyl

(57) ABSTRACT

Process for extracting aqueous ketazine solutions which is carried out using an aqueous ketazine solution having a salt content of 5 to 27% by weight and an ammonia content of 0 to 28% by weight to extract at temperatures of 50 to 120° C., which is characterized in that the ketazine solution to be extracted has a molar excess of 50 to 200% of ketone based on the ketazine to be extracted, and that an aliphatic hydrocarbon extractant is used which has a boiling point of 150 to 300° C. at atmospheric pressure.

12 Claims, No Drawings

EXTRACTION OF KETAZINE SOLUTIONS

BACKGROUND OF THE INVENTION

1. Field of the Invention

The invention relates to a process for extracting aqueous ketazine solutions, in particular for isolating ketazine from aqueous solutions resulting from the preparation of hydrazine.

2. Brief Description of the Prior Art

Hydrazine is prepared according to the "Raschig process" by oxidizing ammonia with sodium hypochlorite. Chloramine is formed as an intermediate and reacts further with excess ammonia to form hydrazine. In one variant of the Raschig process, the "ketone process", ketones are added to the reaction mixture, and ketazines and possibly hydrazines are formed. Acid hydrolysis of the ketazines can convert these to hydrazine and the corresponding ketone. While the syntheses mentioned above can be carried out in good yields, using simple technical means, the workup of the synthesis solutions, i.e. the removal of the hydrazine, hydrazone and ketazine reaction products, is problematic owing to their low concentration and the high content of inorganic salts and organic reaction partners.

When removing ketazines, a distinction needs to be drawn between processes which can be applied to the removal of dimethylketazine (acetone(1-methylethylidene)hydrazone), which results from the use of acetone in the ketone process, and those processes which are suitable for the removal of higher ketazines which are based on ketone having more than 3 carbon atoms.

DE 1 273 503 B discloses that aqueous solutions of dimethylketazine can be worked up to give ketazine with the aid of dimethylketazine-water azeotropic distillation after preceding expulsion of ammonia. The dimethylketazine is subjected to hydrolysis during the azeotropic distillation, so that operation has to be effected under rapid acetone reflux and in the presence of excess acetone. Owing to its high specific energy demand, this process is costly.

Higher ketazines can likewise be removed from aqueous solutions as a result of minimum azeotrope formation using water. Such a process is described, for example, in DE 1 282 617 B. The removal of higher ketazines by means of adding hydrophilic substances, in particular by adding salts, is also possible. This separates the system into two phases, and the aqueous phase can be removed from the phase containing the ketazines. Such a process is described, for example, in DE 2 056 357 B. A disadvantage of the higher ketazines which can be removed relatively easily is that ketones have to be used which cost more than acetone. In addition, the technical and energy demands of the subsequent hydrolysis to give hydrazine and ketone are higher than for dimethylketazine. Workup measures which are effected by the addition of salts increase the resulting salt burden in an undesirable manner.

GB 1 191 630 B discloses an extractive workup of aqueous ketazine solutions. This document describes the preparation of hydrazine from aqueous ketazine- and hydrazone-containing solutions which is based on extractive hydrazone disproportionation. The extractants used are chlorinated hydrocarbons, aromatic solvents such as benzene and toluene and also alcohols, in order to remove the ketazine forming in addition to hydrazine during the disproportionation of hydrazone from the equilibrium. A disadvantage of this process is that the yields of free hydrazine are only about 60%.

DE 24 36 335 A describes a process for working up aqueous synthesis solutions during hydrazine preparation which involves extracting the synthesis solutions to remove ketazine using organic solvents which are water-immiscible or only slightly miscible. The solvents used were higher alcohols, chlorinated hydrocarbons and also optionally substituted aromatics. The document further describes the dependence of the number of extraction stages to attain a maximum hydrazine yield upon various factors such as salt content, ammonia concentration, concentrations of hydrazine, hydrazone and ketazine, temperature, pressure and molar ratio of ketazine to total hydrazine.

A disadvantage of the process mentioned is that the extract obtained, depending on the extractant used, has a relatively high content of water, acetone and salts. The high water content complicates the isolation of the ketazine, while the high acetone content in the extract results in a multistage extraction achieving a reduced molar ratio of ketone to overall hydrazine in the aqueous phase and leads to deterioration in the partition coefficients. A high salt content has to be reduced by subsequent washing, since it otherwise disrupts the distillative workup. A further disadvantage is that the extraction performance of the extractant diminishes in the course of time which leads to undesirable product losses.

There is accordingly a need for a process for extracting ketazines, preferably from synthesis solutions as result from hydrazine preparation, which does not have the abovementioned disadvantages.

SUMMARY OF THE INVENTION

Surprisingly, a process has now been found for extracting aqueous ketazine solutions which is carried out using an aqueous ketazine solution having a salt content of 5 to 27% by weight and an ammonia content of 0 to 28% by weight to extract at temperatures of 50 to 120° C., which is characterized in that the ketazine solution to be extracted has a molar excess of 50 to 200% of ketone based on the ketazine to be extracted, and that an aliphatic hydrocarbon extractant is used which has a boiling point of 150 to 300° C. at atmospheric pressure.

The process according to the invention facilitates in particular the workup of ketazine-containing synthesis solutions as are obtained from hydrazine preparation. Synthesis solutions from hydrazine preparation are reaction mixtures as are obtained from the known processes after the stage of synthesizing hydrazine, hydrazones and ketazines for the purposes of preparing hydrazines or hydrazine derivatives by oxidizing ammonia, which may also be present in the bound form, using an active halogen or peroxy (—O—O—) compound of any type in the presence of further components. Depending on the type of hydrazine preparation, the composition of the synthesis solution may vary. Apart from hydrazine, reaction products of hydrazine with ketones, for example hydrazones, ketazines and water, the following further substances may be present: ammonia, ketones, salt-like compounds, salts and organic components which are necessary for the purposes of the reaction or result from the synthesis, for example nitriles, esters, imides or amides, as are obtained from the known processes which use hydrogen peroxide. Hereinbelow, the molar sum total of hydrazine, hydrazone and ketazine is referred to as total hydrazine. The process according to the invention facilitates the isolation of ketazines and any hydrazones in the form of pure aqueous solutions which can be converted to hydrazine or salts thereof or to other derivatives of hydrazine.

DETAILED DESCRIPTION OF THE INVENTION

In principle, the process according to the invention may be used for aqueous ketazine solutions, in particular for synthesis solutions as obtained from hydrazine preparation by the ketone process, which comprise ketazines and ketones, with or without hydrazones. The ketones (I), ketazines (III) and any hydrazones (II) present preferably correspond to the formulae (I) to (III)

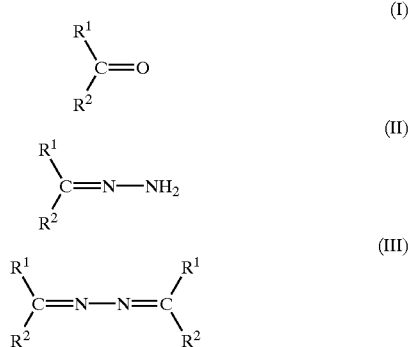

where
- $R^1$ and $R^2$ are each independently straight-chain or branched $C_1$–$C_{12}$-alkyl, $C_3$–$C_{12}$-cycloalkyl or $C_6$–$C_{14}$-aralkyl or
- $R^1$ or $R^2$ is $C_6$–$C_{10}$-aryl or
- $R^1$ and $R^2$ together are a portion of a cyclic system having 5 to 10 carbon atoms.

The aqueous ketazine solutions which are used in the process according to the invention preferably comprise ketazines and ketones, with or without hydrazones, of the formulae (I) to (III) where
- $R^1$ and $R^2$ are each independently methyl, ethyl, n-propyl, isopropyl, phenyl or benzyl or
- $R^1$ and $R^2$ together forms a portion of a cyclohexane or cycloheptane ring.

The aqueous ketazine solutions which are used in the process according to the invention particularly preferably comprise ketones (and the corresponding ketones, with or without hydrazones, derived therefrom according to the formulae (II) and (III)) from the group of acetone, 2-butanone, 2-pentanone, 3-pentanone, methyl isopropyl ketone, methyl benzyl ketone, methyl phenyl ketone, cyclopentanone and cycloheptanone. The aqueous ketazine solutions which are used in the process according to the invention most preferably comprise acetone, and dimethylketazine, with or without acetone hydrazone, derived therefrom according to the formulae (II) and (III).

The homogeneity of the aqueous ketazine solution used in the process according to the invention, in particular of a synthesis solution as obtained from the preparation of hydrazine, is not decisive. Homogeneous solutions, multiphase mixtures, multiphase mixtures containing sediments or mixtures of an aqueous phase with a sediment may be worked up. Preference is given to using homogeneous solutions and multiphase mixtures having an organic and an aqueous phase without sediment.

In the process according to the invention, the aqueous ketazine solutions used comprise a molar excess of 20 to 300% of ketone, preferably 50 to 200% of ketone, more preferably 50 to 150% of ketone, based on the ketazine to be extracted. The ketone is preferably of the formula (I), where the $R^1$ and $R^2$ radicals are identical to the $R^1$ and $R^2$ radicals of the ketazine of the formula (III). The addition of an excess of ketone converts any hydrazine or hydrazone present in the aqueous ketazine solution used to ketazine. The aqueous ketazine solutions used in the process according to the invention preferably have a ketazine content of 0.01 to 5 mol/l, more preferably a ketazine content of 0.01 to 4 mol/l, most preferably a ketazine content of 0.05 to 3 mol/l.

In the process according to the invention, the aqueous ketazine solutions used comprise a salt content of 5 to 27% by weight, preferably 10 to 25% by weight, more preferably 15 to 22% by weight based on total weight of the solution. The salts are salts of inorganic or organic acids or hydroxides of the metals of main groups 1 and 2 of the Periodic Table and also of ammonium. The salts are more preferably NaCl.

In the process according to the invention, the aqueous ketazine solutions used may comprise ammonia. The aqueous ketazine solutions used preferably comprise 0 to 28% by weight of ammonia, more preferably 0 to 20% by weight.

The process according to the invention is carried out at temperatures of 50 to 120° C., preferably at 55 to 100° C., more preferably at 60 to 90° C.

The extractants used in the process according to the invention are aliphatic hydrocarbons which have a boiling point of from 150 to 300° C. at atmospheric pressure. Preference is given to using aliphatic hydrocarbons having 9 to 20 carbon atoms, greater preference is given to using branched alkanes having 9 to 20 carbon atoms, which are preferably in the form of the isomeric mixtures. The preferred isomeric mixture comprises mixtures of isoalkanes and more preferably a mixture of isododecane isomers.

The weight ratio of the extractant used in the process according to the invention to the ketazine solution to be extracted is 1:15 to 3:1, preferably 1:10 to 2:1 and more preferably 1:5 to 1:1.

The process according to the invention is customarily carried out at or above atmospheric pressure, preferably at a pressure of 1 to 3 atm, more preferably at atmospheric pressure.

The process according to the invention may consist of one or more extraction steps, preferably of more than one extraction step, and more preferably—to—extraction step. To determine the theoretical number of extraction steps, a defined volume of the aqueous ketazine solution to be extracted is intensively mixed more than once with the same volume of extractant and the total hydrazine remaining in the aqueous phase is determined. Preference is given to determining the total hydrazine by iodometric titration in a sodium hydrogencarbonate medium after boiling the extractant and the ketone in a strongly acidic medium or using spectroscopic methods, for example proton magnetic resonance or gas chromatography.

The process according to the invention may be carried out batchwise or continuously. Preference is given to carrying it out by the continuous method. In this method, preference is given to intimately mixing the aqueous ketazine solution to be extracted and the extractant. The mixing may be achieved by shaking, stirring or other suitable measures using known equipment.

Preference is given to working up the extract resulting from carrying out the process according to the invention by distillation. Preference is given to distillatively separating the extract under reduced pressure, more preferably at a pressure of from 10 to 200 mbar, to obtain a top product which preferably has a ketazine content of more than 90% by weight and a water content of less than 2% by weight.

The top product may be worked up by known methods, for example by acid hydrolysis with liberation of hydrazine (see DE 24 36 335 A). The bottom product obtained is the extractant which in a preferred embodiment of the process according to the invention is returned to the extraction.

When the extractant used in the process according to the invention is returned to the extraction after removal of the ketazine, preference is given to subjecting it to purification before it is returned. Particular preference is given to subjecting it to scrubbing with dilute, aqueous acid so that it is free of basic nitrogen compounds such as ammonia, ketazines, hydrazine and derivatives thereof and also hydrazones. Particular preference is given to purifying the extractant by steam distillation before it is returned to the reaction.

The process according to the invention is illustrated hereinbelow with the aid of non-limiting examples. The yields are reported in % by weight or in mol % of the quantity used. The compositions of the solutions are reported predominantly in % by weight or the total hydrazine content of the solution is reported in mg/ml or mol/l. The NaCl content in the extract was analysed as mg/kg Na. The content of basic nitrogen compounds (substantially ketazines, hydrazine and derivatives thereof and also hydrazones) was determined by nitrogen analysis, and the result reported in mg/ml of total nitrogen. The ketone used in all examples was acetone, and the ketazine used was dimethylketazine.

EXAMPLES

Example 1

250 g of an aqueous solution containing 6.80% by weight of ketazine, 14.9% by weight of NaCl, 13.7% by weight of ammonia and a molar excess of 50% free acetone, based on ketazine, were intensively stirred with 250 g of isododecane at a temperature of 60° C. over 30 min. The mixture was then left to settle for about 2 min and the phases were separated.

The aqueous phase contained 0.23% by weight of ketazine.

The organic phase contained 6.02% by weight of ketazine, 0.1% by weight of ammonia and 1.99% by weight of acetone.

Comparative Example 1

Comparative Example 1 was carried out in a similar manner to Example 1, except that instead of 250 g of isododecane, 250 g of 2-ethylhexanol were used.

The aqueous phase contained 0.33% by weight of ketazine.

The organic phase contained 5.59% by weight of ketazine, 1.7% by weight of ammonia, 2.74% by weight of water and 3.97% by weight of acetone.

Example 2

250 g of an aqueous solution containing 6.80% by weight of ketazine, 19.6% by weight of NaCl, 13.7% by weight of ammonia and a molar excess of 50% free acetone, based on ketazine, were intensively stirred with 250 g of isododecane at a temperature of 60° C. over 30 min. The mixture was then left to settle for about 2 min and the phases were separated.

The organic phase contained 6.08% by weight of ketazine, 0.1% by weight of ammonia and 0.05% by weight of water and 1.93% by weight of acetone.

Comparative Example 2

Comparative Example 2 was carried out in a similar manner to Example 2, except that instead of 250 g of isododecane, 250 g of 2-ethylhexanol were used.

The aqueous phase contained 0.27% by weight of ketazine.

The organic phase contained 5.65% by weight of ketazine, 1.5% by weight of ammonia, 2.61% by weight of water and 3.90% by weight of acetone.

Example 3

250 g of an aqueous solution containing 6.20% by weight of ketazine, 19.6% by weight of NaCl, 0.54% by weight of ammonia and a molar excess of 50% free acetone, based on ketazine, were intensively stirred with 250 g of isododecane at a temperature of 60° C. over 30 min. The mixture was then left to settle for about 2 min and the phases were separated.

The aqueous phase contained 0.45% by weight of ketazine.

The organic phase contained <1 mg/kg of Na.

Comparative Example 3

Comparative Example 3 was carried out in a similar manner to Example 3, except that instead of 250 g of isododecane, 250 g of 2-ethylhexanol were used.

The aqueous phase contained 0.70% by weight of ketazine.

The organic phase contained 19 mg/kg of Na.

Example 4

Example 4 was carried out in a similar manner to Example 3, except that instead of 250 g of isododecane, 250 g of Isopare® G (isoparaffinic hydrocarbon mixture, commercial product of ExxonMobil Chemical Central Europe GmbH) were used.

The aqueous phase contained 0.53% by weight of ketazine.

Example 5

Example 5 was carried out in a similar manner to Example 3, except that the extraction was carried out at 70° C. in three steps with 250 g of isododecane each time. The aqueous phase was then analysed. After the first extraction stage, the aqueous phase contained 0.64% by weight of ketazine, after the second 0.076% by weight of ketazine and after the third extraction stage 0.022% by weight of ketazine.

Example 6

Example 6 was carried out in a similar manner to Example 5, except that instead of isododecane, the same quantity of triisobutylene was used as extractant. The aqueous phase was then analysed. After the first extraction stage, the aqueous phase contained 0.66% by weight of ketazine, after the second 0.079% by weight of ketazine and after the third extraction stage, the ketazine content was below the detection limit.

Example 7

250 g of an aqueous solution containing 6.30% by weight of ketazine, 19.3% by weight of NaCl, 0.52% by weight of ammonia and a molar excess of 150% free acetone, based on ketazine, were intensively stirred with 250 g of isododecane at a temperature of 60° C. over 30 min. The mixture was then left to settle for about 2 min and the phases were separated.

The aqueous phase contained 0.15% by weight of ketazine.

Example 8

250 g of an aqueous solution containing 6.0% by weight of ketazine, 17.1% by weight of NaCl, 0.49% by weight of ammonia and a 100% molar excess of free acetone, based on ketazine, was continuously extracted in a pulsed randomly packed column using isododecane by the countercurrent principle at a temperature of 65° C. at atmospheric pressure. The volume ratio of aqueous ketazine solution to isododecane was 2:1.

The residence time in the column was 17 min.

The aqueous phase afterwards contained 150 mg/l of total hydrazine.

Example 9

The organic phase obtained by Example 8 was distilled under a reduced pressure of 100 mbar. According to GC analysis, the top product contained 98.7% by weight of ketazine and 0.35% by weight of water. The bottom product was free of ketazine, but according to nitrogen analysis still contained 35 mg/l of total nitrogen.

Example 10

The bottom product from Example 9 was scrubbed using 10% sulphuric acid. The total nitrogen content afterwards was below the detection limit. The isododecane treated in this manner was returned to the extraction. After 5 extraction/distillation cycles, the same total hydrazine contents were found on average in the aqueous phase as when using fresh isododecane.

Example 11

The bottom product from Example 9 was purified by means of steam distillation. The total nitrogen content afterwards was below the detection limit. The isododecane treated in this manner was returned to the extraction. After 5 extraction/distillation cycles, the same total hydrazine contents were found on average in the aqueous phase as when using fresh isododecane.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Process for extracting aqueous ketazine solutions which is carried out using an aqueous ketazine solution having a salt content of 5 to 27% by weight and an ammonia content of 0 to 28% by weight to extract at temperatures of 50 to 120° C., which is characterized in that the ketazine solution to be extracted has a molar excess of 50 to 200% of ketone based on the ketazine to be extracted, and that an aliphatic hydrocarbon extractant is used which has a boiling point of 150 to 300° C. at atmospheric pressure.

2. Process according to claim 1, characterized in that the aqueous ketazine solution is a synthesis solution resulting from the preparation of hydrazine.

3. Process according to claim 1, characterized in that the aqueous ketazine solution contains one or more compounds selected from the group consisting of hydrazine, reaction products of hydrazine with ketones, hydrazones, water, ammonia, ketones, salt-like compounds, salts and organic components.

4. Process according to claim 1, characterized in that the ketazine present is dimethylketazine and the ketone present is acetone.

5. Process according to claim 1, characterized in that the aliphatic hydrocarbons used are mixtures of isomers.

6. Process according to claim 1, characterized in that the mixtures of isomers are mixtures of isoalkanes.

7. Process according to claim 1, characterized in that the aliphatic hydrocarbons used are isododecanes.

8. Process according to claim 1, characterized in that the extraction is carried out in more than one step.

9. Process according to claim 1, characterized in that the extraction is carried out continuously.

10. Process according to claim 1, characterized in that the extract is distilled under reduced pressure to give a top product having a ketazine content of more than 90% by weight and a water content of less than 2% by weight.

11. Process according to claim 10, characterized in that the extractant is obtained as the bottom product, purified and returned to the extraction.

12. Process according to claim 1, characterized in that the salt is NaCl.

* * * * *